United States Patent [19]

Nadolsky et al.

[11] Patent Number: 5,112,603
[45] Date of Patent: May 12, 1992

[54] THICKENING AGENTS FOR AQUEOUS SYSTEMS

[75] Inventors: Richard J. Nadolsky, Clarksburg; Joseph M. Laryea, Old Bridge, both of N.J.

[73] Assignee: Miranol Inc., Dayton, N.J.

[21] Appl. No.: 292,510

[22] Filed: Dec. 30, 1988

[51] Int. Cl.$^5$ .................. A61K 31/10; A61K 31/74
[52] U.S. Cl. .................. 514/772.3; 424/70; 424/62; 424/63; 528/310; 525/418; 524/606; 524/5; 524/446; 106/468; 252/106; 252/8.551; 507/117
[58] Field of Search .............. 424/78, 70, 62, 63; 528/310; 525/418; 524/606; 106/468; 252/8.551, 8.514, 8.515, 106

[56] References Cited

U.S. PATENT DOCUMENTS

| | | | |
|---|---|---|---|
| 4,157,388 | 6/1979 | Christiansen | 528/390 |
| 4,436,862 | 3/1984 | Tetenbaum et al. | 524/445 |
| 4,505,833 | 3/1985 | Lipowski | 252/8.55 |
| 4,517,174 | 5/1985 | Jacquet et al. | 424/62 |
| 4,659,571 | 4/1987 | Laba | 424/63 |
| 4,677,158 | 6/1987 | Tso et al. | 524/445 |
| 4,695,402 | 9/1987 | Finlayson et al. | 523/508 |
| 4,719,282 | 1/1988 | Nadolsky et al. | 528/310 |

Primary Examiner—Lester L. Lee
Assistant Examiner—E. J. Kraus
Attorney, Agent, or Firm—Ladas & Parry

[57] ABSTRACT

The present invention relates to compositions useful as thickening agents for aqueous systems. More particularly, it relates to compositions comprising smectite clays and cationic polymers.

22 Claims, No Drawings

THICKENING AGENTS FOR AQUEOUS SYSTEMS

BACKGROUND OF THE INVENTION

1. Field of the Invention

The present invention relates to compositions usefule as thickening agents for aqueous sytems. More particularly, it relates to compositions comprising smectite clays and cationic polymers.

2. Description of the Prior Art

U.S. Pat. No. 4,157,388 (Christiansen issued June 5, 1979) describes a variety of cationic polymers. A typical product according to that patent is of the formula:

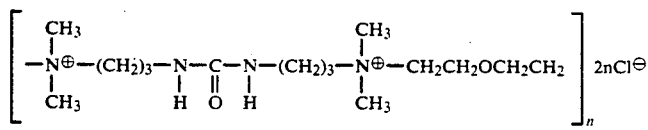

wherein n is at least one.

The products are stated to be of use as conditioning agents in shampoos, as anti-static and humectants for fibrous textile products and anti-dusting agents for powders.

In commonly assigned copending application Ser. No. 758,483 filed on Jul. 24, 1985 which is a continuation-in-part of application Ser. No. 458,197 filed on Aug. 15, 1983, there are described products of the general Formula:

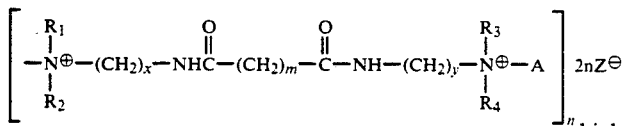

wherei $R_1$, $R_2$, $R_3$, and $R_4$ may be the same or different and select the group consisting of hydrogen, methyl, ethyl, propyl, —$CH_2CH_2OH$, —$CH_2CH(OH)CH_3$ and —$CH_2CH_2(OCH_2CH_2)pOH$ wherein p is an integer from 0 to 6 with the proviso that not all of $R_1$, $R_2$, $R_3$ and $R_4$ are hydrogen;

x and y are the same or different and are an integer from 1 to 6;

n is a value such that the number average molecular weight of the product is in excess of 20,0000;

m is an integer from 0 to 34, for example, 3-10, typically 4-7;

X is halogen;

Z is halogen or amino-diamido ammonium residue; and

A is the residue of a dihalide.

U.S. Pat. No. 4,719,282 (Nadolsky et al) describes certain block copolymers of the formula:

[(2[x + y)]⊕

[$Q_wL(AL)_x(BL)yAQ_w$]   2(x + y)D⊖ wherein A is

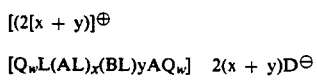

and B is

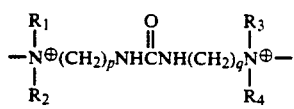

-continued

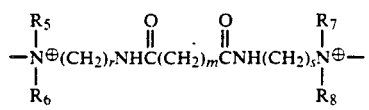

wherein:

$R_1$, $R_2$, $R_3$, $R_4$, $R_5$, $R_6$, $R_7$, and $R_8$ are the same or different and are generally selected from the group consisting of $C_1$-$C_3$ alkyl, $C_1$-$C_3$ hydroxyalkyl, or hydroxy polyoxy-alkylene;

D is a halide ion;

L is a linkage derived from a dihalide after removal of the halogen atoms, x and y are integers ranging from 1-100, m is an integer from 0 to 34, p, q, r and s are the same or different and are integers from 1 to 6, and Q is (BL)y where the bonds between L and A or B are carbon-nitrogen bonds formed by quaternization of the tertiary amine functions of A and B by the organic dihalides from which L is derived and w is 0 or 1 which are obtained by first forming a block of units by reacting a monomer of the formula II

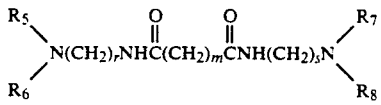

wherein each of $R_5$, $R_6$, $R_7$, and $R_8$ are the same or different and is selected from the group consisting of $C_{1-3}$ alkyl, $C_{1-3}$ hydroxy alkyl and hydroxy polyoxyalkylene, with a molar excess of a dihalide of the formula:

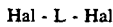

Hal - L - Hal wherein Hal represent a halogen atom and L is selected from —$_2CH_2$—O—$_2CH_2$—, —$_2CH_2$—O—$_2C$-$H_2$—O—$_2CH_2$—, —$(CH_2)t$—and —$CH_2CHOHCH_2$—- where t is an integer from 2 to 6 and thereafter reacting the product so formed with a compound of the formula III

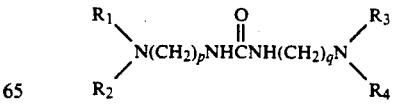

wherein $R_1$, $R_2$, $R_3$, and $R_4$, are each individually selected from the group consisting of $C_{1-3}$ hydroxyalkyl and hydroxy polyoxyalkylene and p, and q are each individually integers of from 1 to 6 and, if necessary, in order to ensure a total molar ratio of compounds of Formulae II and III to those of the formula Hal - L - Hal of 1:1, reacting the product with further compound of the formula Hal - L - Hal.

These products are stated to be of use as anti-static-aids in detergent formulations and as flocculating agents. Example 7 describes a clay compaction test using such block copolymers at low concentrations with Accugel F, a smectite-type clay at a pH of 5.0 5.9 in which it was found that at these pH's the block copolymer had a compacting effect on the clay.

U.S. Pat. No. 3,734,889 (Lipowski issued May 22, 1973) describes the use of a polymer obtained by condensing polyamines having one primary amino group and one tertiary amino group with a chain extender to produce products useful as flocculents, drainage aids and dry strength resins in paper manufacture, for example, to assist in removal of fillers and fines used in the paper making process.

U.S. Pat. No. 4,505,833 (Lipowski issued Mar. 19, 1985) describes the use of quaternized oligomers, including those obtained by reacting dimethyl amino propylamine with a dicarboxylic acid to prevent, inhibit or reduce swelling or migrating of clay particles including swelling clays such as smectites in a clayey geological formation. Results are reported of the effects at a pH of about 5.9.

U.S. Pat. No. 4,247,476 (Haase et.al. issued Jan. 27, 1981) describes a certain type of polymeric quaternary ammonium salts which are stated to be of use as dying and finishing agents in the textile industry and as dispersing agents and emulsifiers as anti-static anti microbial and flocculating agents and as precipitants.

Jacquet U.S. Pat. No. 4,517,174 describes cosmetic uses for a wide variety of polycationic polymers. Similar uses for certain bis(quaternary ammonium) derivatives are described in Zorayan's U.S. Pat. No. 4,612,188.

U.S. Pat. Nos. 4,536,305 (Borchadt et.al.) and 4,563,292 (Borchadt) describe the use of polymeric materials having side chains containing quaternary ammonium groups for use in treating formations containing smectite-type swelling clays to render them less swelling thereby facilitating the extraction of oil or gas from geological formulations in which such clays occur. This is effected by replacing ions present in the clay by potassium, calcium, ammonium and hydrogen ions that render the clays less swelling. The polycationic polymers are stated to be helpful in retaining replacement ions in place.

U.S. Pat. No. 4,532,052 (Weaver et.al.) describes several new treatment processes and compositions for practicing them. These processes substantially alter the fluid flow and surface characteristics of porous permeable particular formations, especially subterranean formations intersected by an oil well. The compositions of this invention also provide methods of increasing viscosity or gelling aqueous fluids, especially acids, which can be used to treat such earthen formations. A wide variety of polymers is described including branched organic polymers of a wide molecular weight range. The branches are preferably hydrophilic and the polymer contains bonding groups (e.g., ionic bonding groups) which serve to attract or repel a substrate, a particular formation, suspended solids, other polymers or segments, carrier fluid or a fluid to be treated.

U.S. Pat. No. 4,390,689 (Jacquet et.al. issued June 28, 1983) describes a variety of polycationic polymers that are said to be useful in the treatment of hair and skin and natural and synthetic fibers.

U.S. Pat. No. 4,695,402 (Finlayson et.al. issued Sept. 22, 1987) describes organophilic clay gellants prepared by a process wherein the smectite-type clay is subjected to shearing in order to break apart the agglomerates and/or the smectite-type clay and reacted with organic cation and, possibly organic anion, under dilute reaction conditions. The reaction product is recovered using gentle drying conditions. Depending in large part on its composition, the organophilic clay gellant may be used to thicken a variety of organic compositions. It is stated that in a preferred aspect, the organophilic clay gellant can be directly added to polyester compositions in order to efficiently and effectively increase the viscosity thereof or can be first formed into a pregel under low shear conditions to yield even higher efficiencies. The cationic materials employed include monomeric ammonium salts such as benzyl dimethyl hydrogenated tallow ammonium chloride. However, no suggestion is made of any use of polymeric cationic materials.

U.S. Pat. No. 3,594,212 (Ditsch issued Jul. 20, 1971) described the treatment of cotton fibrous material with an alkali metal or acid montmorillonite clay with a polyamine or polyquaternary ammonium compound to impart softness. It is stated that any montmorillonite clay can be used and any polyamine or polyquaternary ammonium compound that is water soluble. However, polyimines are preferred. Polymers of the type described in U.S. Pat. No. 3,594,212 are discussed in U.S. Pat. No. 4,141,691 (Antonetti et.al., issued Feb. 27, 1979). This indicates that such polymers may have a flocculating effect on clays.

U.S. Pat. No. 4,677,158 (Tso et.al.) describes the use of a high molecular weight polyethoxylated quaternary ammonium monomer compound to treat certain smectite clays to render them useful as thickeners for aqueous suspension such as latex paints.

U.S. Pat. Nos., 4,610,801 and 4,711,727 (Matthews et. al. issued Sept. 9, 1986 and Dec. 8, 1987 respectively) describe the slurrying of mineral particles possibly including a synthetic hectorite by using as flocculating agents various cationic and amphoteric polyelectrolytes such as polyamines. The slurries are stated to be useful in paper making and the treatment of sewage.

U.S. Pat. No. 4,365,030 (Oswald et.al. issued Dec. 21, 1982) describes higher dialkyl dimethyl ammonium clays of use as gellants of use for example in alkyd resin based coatings.

Another organophilic clay gellant is described in U.S. Pat. No. 4,412,018 (Finlayson et.al. issued Oct. 25, 1983). The product is a smectite type clay into which organic cations and anions have been intercalated. Among the possible cations mentioned are quaternary ammonium compounds.

Another gellant of this type is described in U.S. Pat. No. 4,434,076 (Mardis et.al. issued Feb. 28, 1984). In this case, a smectite-type clay is reacted with an organic cationic compound, such as a quaternary ammonium compound that possesses at least one $\beta,\alpha$ unsaturated alkyl group or a hydroxyalkyl group of 2-6 carbon atoms, a long chain alkyl group and one or two relatively short chain alkyl groups.

U.S. Pat. No. 2,873,251 (Jones issued Feb. 10, 1959) describes the use of polyamines in drilling muds. Bentonite type clays may be pressed in the mud.

U.S. Pat. No. 2,807,910 (Erickson issued Oct. 1, 1957) describes the addition of polyquaternary ammonium compound as soil conditioners.

Organo-clay complexes are marketed under the tradename Bentone. Such complexes are made from simple monoquaternary ammonium salts, possessing one or more fatty alkyl groups on the quaternary nitrogen, and a smectite type clay. These complexes are lipophilic and are widely used to thicken oil-based systems such as alkyd paints, oil-based drilling muds and certain cosmetic formulations. They are generally formed under very specific conditions in aqueous media, then isolated, dried and marketed as solid products.

BRIEF DESCRIPTION OF THE PRESENT INVENTION

We have now found that the combination of certain types of polyquaternary compounds with smectite clays produces very useful thickening agents for use in aqueous systems. Such agents are useful for thickening personal care formulations such as creams and lotions, as well as make-up bases. Other potential applications are in latex paint, aqueous hydraulic fluids, drilling muds, and concrete additives. In the latter application, these complexes could serve to decrease the concrete's density and prolong the drying time, thus decreasing the tendency to form cracks.

The polyquaternary compounds of use in the present invention are those that comprise the repeating group

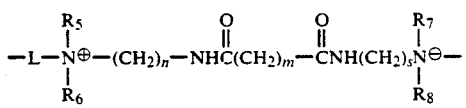

wherein $R_5$, $R_6$, $R_7$ and $R_8$ may be the same or different and are selected from the group consisting of $C_{1-3}$ alkyl, $C_{1-3}$ hydroxy alkyl or polyoxy alkylene, L is a linking group derived from a dihalide, m is an integer from 0 to 34, but is preferably at least 1, typically 4–7 for example about 6 and r and s are the same or different and are integers of from 1 to 6.

Typical L groups are those of the formula —CH$_2$CH$_2$—(OCH$_2$CH$_2$)$_u$—OCH$_2$CH$_2$ wherein u is 0 or 1, (CH$_2$)$_t$ where t is from 2 to 6 and —CH$_2$CH(OH)CH$_2$—.

Such units may comprise the sole repeating units in the polymer or they may be present together with units of the formula:

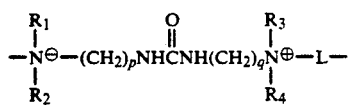

wherein $R_1$, $R_2$, $R_3$ and $R_4$ may be the same or different and are selected from the group consisting of $C_{1-3}$ alkyl, $C_{1-3}$ hydroxyalkyl or polyoxyalkylene, p and q are each integers from 1-6 and L is a linkage group derived from a dihalide. When such additional units are present the product may be in the form of a block or random copolymer.

Accordingly from the first aspect, the present invention comprises a thickening agent comprising a mixture of a smectite clay and a polyquaternary ammonium polymer comprising repeating units of the formula:

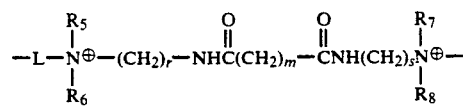

wherein $R_5$, $R_6$, $R_7$, $R_8$, m, r, s and L are as defined above.

From a second aspect, the present invention comprises a method for preparing such a thickening agent by subjecting an aqueous mixture of a smectite clay and a polymer of the specified type to mixing conditions, preferably at high shear.

From a third aspect, the present invention provides a latex paint composition containing a thickening agent of the type described and from a fourth aspect it provides a cosmetic composition containing a thickening agent of the type described.

Without wishing to be bound by any theory, we believe that the usefulness of the thickening agents of the present invention lies in the ability of the particular polyquaternary compounds used in the present invention to cause the smectite clays to swell and increase the hydration of the clay. This phenomenon is apparent at pH's above about 6.5 and more particularly at pH's above 7. It appears that the gel structure of the polymer/clay structure that is stable in alkali conditions breaks down if the system becomes acid to a significant extent. This contrasts, for example, with the effect of the polyquaternaries used in U.S. Pat. No. 3,594,212 whose role is to cause flcccula-tion or the product of U.S. Pat. No. 4,157,388 which our tests have shown cause compaction rather than swelling of the clay.

DESCRIPTION OF THE PREFERRED EMBODIMENTS

The polyquaternary polymers for use in the present invention are preferably of the type described in commonly assigned copending application 758,483 or in commonly assigned U.S. Pat. No. 4,719,282.

The polymers of application 758,483 are of the formula:

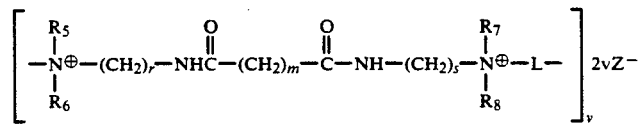

wherein $R_5$, $R_6$, $R_7$ and $R_8$ are each selected from the group consisting of $C_1$–$C_3$ alkyl. r and s are each integers from 1-6, typically 3, and m is from 0 to 34, normally at least 1 and commonly 4–7 for example about 6. v has an average value of greater than 50, preferably 70–140, typically about 110–120. L is a linking group and is commonly a residue of an alkylene dihalide such as ethylene dichloride or a dihalogenated ether such as 2,2'-dichloro diethyl ether. Z is halogen. The production of such polymers is described in copending application 758,483 and its corresponding published European counterpart, European Patent 1222324 both of which are herein incorporated by reference. Such polymers typically have a number average molecular weight in excess of 20,000 typically in the range 40,000 to 55,000. These products are prepared by condensing two moles of an N,N-disubstituted alkylene diamine with a dicarboxylic acid and subsequently quaternizing this with a compound of the formula Hal-L-Hal wherein Hal is a halo atom such as chloro. These products differ from the polyquaternaries described in U.S. Pat. No. 4,505,833 in that the products described in that patent are apparently of relatively low molecular weight and are produced by a different means that will result in their having different impurity contents.

Polymers according to U.S. Pat. No. 4,719,282 are block copolymers of the formula:

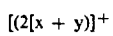

wherein A is

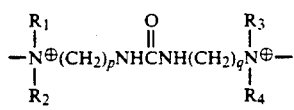

and B is

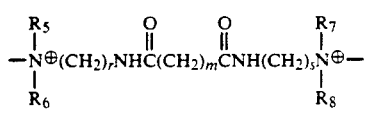

wherein:

$R_1$, $R_2$, $R_3$, $R_4$, $R_5$, $R_6$, $R_7$, and $R_8$ are the same or different and are generally selected from the group consisting of $C_1-C_3$ alkyl, $C_1-C_3$ hydroxyalkyl, or hydroxy polyoxy-alkylene;

D is a halide ion;

L is a linkage derived from a dihalide, after removal of the halogen atoms, x and y are integers ranging from 1–100, m is an integer from 0 to 34, p, q, r and s are the same or different and are integers from 1 to 6, and Q is (BL)y where the bonds between L and A or B are carbon-nitrogen bonds formed by quaternization of the tertiary amine functions of A and B by the organic dihalides from which L is derived and w is 0 or 1 which are obtained by first forming a block of units by reacting a monomer of the formula II

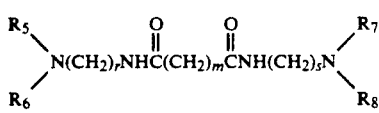

wherein each of $R_5$, $R_6$, $R_7$, and $R_8$ are the same or different and is selected from the group consisting of $C_{1-3}$ alkyl, $C_{1-3}$ hydroxy alkyl and hydroxy polyoxyalkylene, with a molar excess of a dihalide of the formula:

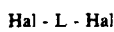

wherein Hal represent a halogen atom and L is selected from $-_2CH_2-O-_2CH_2-$, $-_2CH_2-O-_2CH_2-O-_2CH_2-$, $-(CH_2)_t-$ and $-CH_2CHOHCH_2-$ where t is an integer from 2 to 6 and thereafter reacting the product so formed with a compound of the formula III

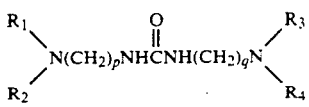

wherein $R_1$, $R_2$, $R_3$, and $R_4$, are each individually selected from the group consisting of $C_{1-3}$ hydroxyalkyl and hydroxy polyoxyalkylene and p, and q are each individually integers of from 1 to 6 and, if necessary, in order to ensure a total molar ratio of compounds of Formulae II and III to those of the formula Hal - L - Hal of 1:1, reacting the product with further compound of the formula Hal - L - Hal.

Such polymers conveniently contain B and A units in a ratio 0.66 to 19:1 more preferably 3 to 9:1.

The $R_1$, $R_2$, $R_3$, $R_4$, $R_5$, $R_6$, $R_7$ and $R_8$ groups are briefly all alkyl, for example, methyl or ethyl. Typically p, q, r and s are from 2 to 4 and m is from 4–7. Such polymers typically have a molecular weight in the range 20,000 to 50,0000.

The production of such block copolymers is described in U.S. Pat. No. 4,719,282, which is incorporated herein by reference. There will now be described production of particularly useful compounds namely those wherein recurring group A is derived from a monomer of the formula

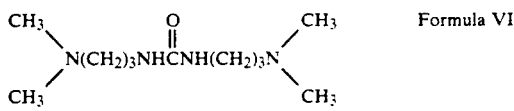

Formula VI recurring group B is derived from a monomer of the formula

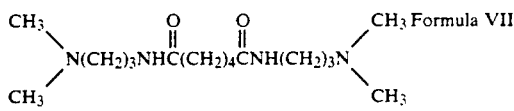

Formula VII and L is $-CH_2CH_2-O-CH_2CH_2-$.

It will, however, be appreciated that the techniques described herein are equally applicable to the production of copolymers wherein A, B and L have different values.

Typically a monomer of formula VII is heated in an aqueous medium to from 60°–100° C., preferably about 90°–100° C. and a molar excess of 2,2'-bis chloroethyl ether added slowly, typically over a period of one to three hours. The excess of the dichloro ether should not exceed 25% but will depend upon the ratio of A and B units in the final product, so that if the ratio of B to A is 0.66 : 1 a 25% molar excess of the dichloro ether may be used whereas if the final ratio of B to A units is 19 : 1 a molar excess of the dichloro ether of only about 10% will be satisfactory. Once addition of the dichloroether has been completed, heating of the reaction mixture is continued for several hours (typically 6 to 10 hours). Monomer of formula VI is then added followed by additional 2,2'-bis (chloroethyl)ether in an amount to result in a 1:1 molar ratio of said ether to the total number of moles of monomers of formulae VI and VII. The reaction mixture is then maintained at elevated temperature, typically in the range of 90° to 100° C. until the ratio of ionic chloride to total chloride exceeds 0.99:1. Such a determination of the amount of ionic chloride can be made, for example by potentiometric titration.

Generally, reactions are conducted in such a way that virtually all of the organic dihalide is consumed or removed from the product. In this way essentially all end groups of the polymer chains are tertiary amino groups. A variant of this procedure may be used when the ratio of monomer of formula VII used to monomer of formula VI exceeds 9:1. In that case all of the 2,2'bis (chloroethyl) ether may be added to the compound of formula VII before addition of compound of formula VI.

Typical products according to the invention have a molar ratio of B to A units in the range 1:1 to 9:1.

Smectites used in the present invention can be of either the dioctahedral or trioctahedral types and include materials such as montmorillonite, spornite, bentonite, nontronite, beidellite, sauconite and hectorite.

Suitable smectites include but are not limited to those sold under the trademarks VANGEL ES and VEEGUM HV (VANGEL AND VEEGUM are trademark of RT Vanderbilt Company, Inc. of Norwalk, Conn.).

The ratio of water:clay:cationic polymer that may be used may vary over a wide range depending on the exchange capacity of the clay, the desired viscosity and desired rheology of the final formulation. Typically, the ratio of smectite to the polymeric quaternary compound in the thickening agents of the present invention is from 1 to 20:1, preferably 1 to 5:1 by weight.

The compositions of the invention should have a pH of at least 6.5, preferably 7 or more. For example, compositions may have a pH in the range 8-10, often about 9. This pH will typically be the result of the presence of components of the composition, for example, components of a cosmetic composition. If necessary, however, pH may be raised by adding other alkaline components compatible with the intended use of the thickening agent.

The thickening agents of the invention frequently employ a smectite that has been subjected to high speed shear. This may be effected by subjecting a mixture of the smectite and the polymeric quaternary compound to high speed shear.

An alternative, but less preferred method for producing the thickening of the present invention is to effect high speed shear of the smectite prior to addition of the polymeric quaternary compound. In this case, it will then take a longer time to achieve maximum viscosity when the polymer is added after applying shear. Adding the polymer before homogenizing the mixture results in much more rapid hydration of the clay giving a particle-free dispersion within 1-2 minutes.

The thickening agents of the present invention may be employed in a wide variety of aqueous systems. Smectite clays are often used for such purposes. The improved swelling of the products of the present invention enables them to be used as a replacement for untreated smectites in any situation wherein such improved swelling is useful. For example, together with an anionic, nonionic, amphoteric or cationic detergent—they may be employed in cleansing compositions such as shampoos and cleansing creams and lotions, for example, skin care creams, liquid soaps and facial make-up removal lotions. In such cases, the thickener will normally be present in from about 1.0 to 8.0 percent by weight of the final formulation, although products may be shipped in a more concentrated form. They may also find use in latex paints such as vinyl acetate and vinyl acrylic latex paints. Thickening agents according to the invention are usefully present in amounts of from 0.1 to 1.5 percent by weight of the paint, although in some cases different concentrations may be appropriate.

The invention will now be more clearly understood by reference to the following examples which are set forth as being merely illustrative of the invention and which are not intended, in any manner, to be limitative thereof.

EXAMPLES 1-2

A hydrophilic organo-clay complex was formed using 0 1.0% and 2.0% of various MIRAPOLSR with Vangel ES. MIRAPOLR is the tradename for high charge cationic polymers available from Miranol Inc.

The caly Vangel ES has a cationic exchange capacity of 5-15 meq/100 g. Viscosities, in centipoise, of these complexes are tabulated below. For comparison, viscosities are also given for various concentrations of Vangel ES in water (i.e., no MIRAPOL ® present).

|  | % VANGEL ES | | | | |
|---|---|---|---|---|---|
|  | 2.5 | 5.0 | 7.0 | 8.0 | 10.0 |
| 1.0% MIRAPOL ® | | | | | |
| None | 800 | 1,000 | 1,350 | 1,550 | 1,800 |
| AD-1 | 3,200 | 22,500 | 35,000 | 40,000 | >100,000 |
| AZ-1 | 1,500 | 4,500 | — | 28.000 | — |
| 95 | 3,400 | 22,500 | 36,500 | 41,000 | >100,000 |
| 9 | 3,700 | 40,000 | 68,000 | >100,000 | >100,000 |
| 175 | 4,200 | 48,000 | 87,000 | >100,000 | >100,000 |
| 2.0% MIRAPOL ® | | | | | |
| None | 800 | 1,000 | 1,350 | 1,550 | <1,800 |
| AD-1 | 2,500 | 15,000 | 22,000 | 32,000 | 75,000 |
| AZ-1 | — | 3,500 | — | 12,000 | — |
| 95 | 2,600 | 15,000 | 23,000 | 33,000 | 77,000 |
| 9 | 2,800 | 6,000 | 26,000 | 36,000 | 87,000 |
| 175 | 3,200 | 5,000 | 29,000 | 40,000 | 92,000 |

MIRAPOL ® AD-1 is the cationic polymer from adipic acid described in U.S. Application 758.483.
MIRAPOL ® AZ-1 is the cationic polymer from azelaic acid described in U.S. Application 758.483.
MIRAPOL ® 9 is the block copolymer described in Example 2 of U.S. Pat. No. 4,719,282.
MIRAPOL ® 95 is the block copolymer described in Example 2 of U.S. Pat. No. 4,719,282 except that it contains 0.95 moles of Condensate B and 0.05 moles of Condensate A.
MIRAPOL ® 175 is the block copolymer described in Example 3 of U.S. Pat. No. 4,719,282.

EXAMPLE 3

In addition, complexes were prepared from MIRAPOLS ® and Veegum HV which is a different grade of smectite clay having a cationic exchange capacity of 75-85 meq/100 g. Various amounts of Veegum HV by itself in water gave the following viscosities (in centipoise):

| % VEEGUM HV | 2.0 | 3.0 | 4.0 | 5.0 | 6.0 | 8.0 | 10.0 |
|---|---|---|---|---|---|---|---|
| Viscosity | 100 | 500 | 1,000 | 2,500 | 4,000 | 45,000 | 80,000 |

EXAMPLE 4

Using 2.0% Veegum HV with 0.5% and 1.0% MIRAPOL ®, the following viscosities were obtained:

| MIRAPOL ® | 0.5% | 1.0% |
| --- | --- | --- |
| AD-1 | 4,500 | 6,000 |
| AZ-1 | 1,000 | 4,000 |
| 95 | 4,000 | 5,000 |
| 9 | 6,500 | 9,000 |
| 175 | 8,000 | 11,000 |

Using 10% Veegum HV and from 0.8 to 3.2% of the above MIRAPOLS ®, all viscosities were greater than 100,000 centipoise.

EXAMPLE 5

With 5.0% Veegum HV, the various MIRA-POLS ®, at levels shown below, give the viscosities indicated:

| MIRAPOL ® | 0.4% | 0.8% | 1.6% |
| --- | --- | --- | --- |
| AD-1 | 8,000 | 12,000 | 26,000 |
| AZ-1 | 13,500 | 25,500 | 36,000 |
| 95 | 7,500 | 12,000 | 23,000 |
| 9 | 11,000 | 17,500 | 28,000 |
| 175 | 14,000 | 30,000 | 42,500 |

EXAMPLES 6-8

Unstable systems were obtained in all cases using either Vangel ES or Veegum HV with the following materials:

Polyguaternium-2 which is a polymeric quaternary ammonium salt that generally conforms to the following structure and is available as MIRAPOL ® A-15.

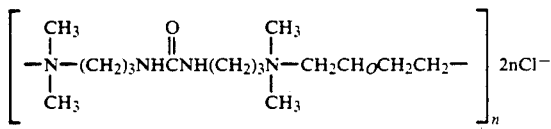

Polyguaternium-6 which is a polymer of dimethyl diallyl ammonium chloride and is available as MERQUATR ® 100

Polyouaternium-7 which is the polymeric quaternary ammonium salt consisting of acrylamide and dimethyl diallyl ammonium chloride monomers and is available as MERQUAT ® 550.

Another advantage to the use of these selected MIRAPOLS ® with clays is that they not only build higher viscosity in water for a given amount of clay, but they significantly increase the rate of hydration of the clay. Using high shear equipment (e.g. homogenizer) it takes 15 to 30 minutes to fully hydrate the VANGEL ES (clay). However, if the clay is added to water using a homogenizer and this is immediately followed by the addition of MIRAPOLR, complete hydration (i.e., a particle-free dispersion) is obtained in 1-2 minutes.

The following examples demonstrate the effect of the MIRAPOL ®/clay combination compared to use of clay alone.

EXAMPLE 9

Use in Skin Cream

|  | F | G |
| --- | --- | --- |
| A |  |  |
| MIRANOL ESTER PO-LM4 (1) | 5.0 | 5.0 |
| Mineral Oil | 20.0 | 20.0 |
| Arlacel 165 [ICI AMERICAS] (2) | 2.5 | 2.5 |
| Stearyl Alcohol | 0.5 | 0.5 |
| B |  |  |
| Deionized Water | 69.5 | 68.5 |
| Vangel ES [R. T. Vanderbilt] | 2.5 | 2.5 |
| MIRAPOL AD-1 | — | 1.0 |

(1) CTFA name: Polypentaerythrityl Tetralaurate
(2) CTFA name: Glyceryl Stearate (and) PEG-100 Stearate Procedure: Premix A was heated to 75° C. with mixing. After homogenization Premix B was added to Premix A with agitation. Agitation was continued until uniform and the mixture was then allowed to cool to room temperature.

OBSERVATION

F = Unstable
G = Sable

EXAMPLE 10

| A |  |
| --- | --- |
| MIRANOL ESTER PO-LM4 | 5.0 |
| Mineral Oil | 10.0 |
| Cerasynt SD (glyceryl Stearate) | 5.0 |
| Stearyl Alcohol | 0.5 |
| Cetyl Alcohol | 0.5 |
| B |  |
| Deionized Water | 67.0 |
| Veegum HV (Magnesium Aluminum Silicate) | 3.0 |
| MIRAPOL 95 | 1.0 |
| C |  |
| MIRANOL C2M-conc. SF (1) | 8.0 |

(1) CTFA name: Cocoamphodipropionate

Procedure: Premix A was heated to 75° C. Premix B was heated to 50° C. and homogenized to ensure uniformity. A was added to B and then C with agitation. Agitation was continued until uniform and the resulting mixutre was then allowed to cool to room temperature.

EXAMPLE 11

Use in Liquid Soap

|  | A | B | C |
| --- | --- | --- | --- |
| I. |  |  |  |
| MIRANOL C2M CON N.P.-LV (1) | 20.0 | 20.0 | 20.0 |
| Potassium Laurate (25% Soln.) | 35.0 | 35.0 | 35.0 |
| Lauramide DEA | 2.0 | 2.0 | 2.0 |
| Cerasynt IP [VAN-DYK] (2) | 1.0 | 1.0 | 1.0 |
| II. |  |  |  |
| Deionized Water | 42.0 | 39.0 | 38.0 |
| MIRAPOL AD-1 | — | — | 1.0 |
| Vangel ES [R. T. Vanderbilt] | — | 3.0 | 3.0 |

(1) CTFA name: Cocoamphodiacetate
(2) CTFA name: Glycol Stearate (and) Other Ingredients Procedure: Premix II was prepared using an homogenizer to assure uniformity. Premix I was heated to 75° C. and mixed until uniform. It was cooled to 50° C. and pH adjusted to 7.8. Premix II was added and mixed until uniform and then allowed to cool to room temperature.

| PROTOTYPE | VISCOSITY |
|-----------|-----------|
| A | 500 cP |
| B | 4,800 cP |
| C | 10,000 cP |

EXAMPLE 12

The following illustrtes the effect of adding the ctionic polymer before applying shear.

| | A | B | C |
|---|---|---|---|
| Deionized Water | 94.0 | 94.0 | 95.0 |
| Vangel ES | 5.0 | 5.0 | 5.0 |
| MIRAPOL AD-1 | 1.0 | 1.0 | |
| Viscosity (1 hr. after mixing) | 34,000 cP | 16,500 cP | 500 cP |

In A, the clay/water was subjected to mixing with the homogenizer for 30 minutes then MIRAPOL AD-1 was added and the mixture homogenized for 5 minutes. In B, after 30 minutes homogenizing the clay/water, MIRAPOL AD-1 was added and mixed for 5 minutes by hand using a stirring rod. In C, the clay/water was homogenized for 30 minutes.

A viscosity of 22,500 cP for 1.0% MIRAPOL AD-1, 5.0% Vangel ES and 94.0% water is shown in Example I. This viscosity was measured immediately after homogenizing the sample. The sample, after standing for 2 months, had a viscosity of 100,000cP. For the examples cited above, after standing overnight, the viscosities were: A=47, 500cP, B=38,000 cP, C=750cP. A sample having the same composition as C that was made about 2 months before had an initial viscosity of 1,000cP which was unchanged after 2 months. From this, it appears that it is not necessary to have the cationic polymer present before applying shear, but that it will then take a longer time to achieve maximum viscosity when the polymer is added after applying shear. In addition, adding the polymer before homogenizing the mixture results in much more rapid hydration of the clay giving a particle-free dispersion with 1-2 minutes.

We claim:

1. An aqueous thickening composition having a pH of at least 6.5 comprising a smectite clay in combination with a quaternary ammonium polymer comprising a repeating unit of the formula:

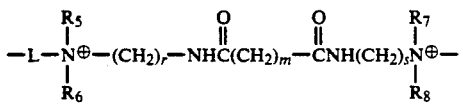

wherein $R_5$, $R_6$, $R_7$ and $R_8$ may be the same or different and are selected from the group consisting of $C_{1-3}$ alkylm $C_{1-3}$ hydroxy alkyl or polyoxy alkylene, L is a linking group derived from a dihalide, m is an integer from 0 to 34, and r and s are the same or different and are integers from 1 to 6.

2. An aqueous composition comprising a thickening agent as claimed in claim 1 wherein the smectite is a sheared smectite.

3. An aqueous composition according to claim 2 wherein said quaternary ammonium polymer is one wherein substantially all of the repeating units are of the said formula:

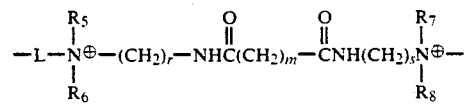

wherein $R_5$, $R_6$, $R_7$ and $R_8$ may be the same or different and are selected from the group consisting of $C_{1-3}$ alkyl, $C_{1-3}$ hydroxy alkyl or polyoxy alkylene, L is a linking group derived from a dihalide, m is an integer from 0 to 34, and r and s are the same or different and are integers from 1 to 6.

4. An aqueous thickening composition according to claim 1 having a pH of at least 7.

5. An aqueous composition according to claim 3 wherein the quaternary ammonium polymer has a molecular weight of 40,000 to 55,000.

6. An aqueous composition according to claim 3 wherein $R_5$, $R_6$, $R_7$ an $R_8$ are each selected from methyl- and ethyl.

7. An aqueous composition according to claim 3 wherein r and s are from 2 to 4.

8. An aqueous composition according to claim 3 wherein m is from 4 to 7.

9. An aqueous composition according to claim 3 wherein the repeating units are of the formula:

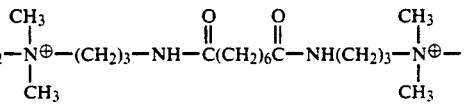

wherein Y is $(CH_2)_2O$.

10. An aqueous composition according to claim 1 wherein said quaternary ammonium polymer is a block copolymer of the formula:

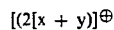

wherein A is

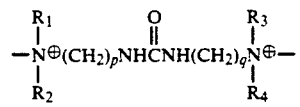

and B is

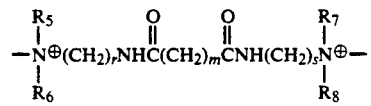

wherein
$R_1$, $R_2$, $R_3$, $R_4$, $R_5$, $R_6$, $R_7$, and $R_8$ are the same or different and are generally selected from the group consisting of $C_1$-$C_3$ alkyl, $C_1$-$C_3$ hydroxyalkyl, or hydroxy polyoxy-alkylene;

D is a halide ion;

L is a linkage derived from a dihalide after removal of the halogen atoms, x and y are integers ranging from 1–100, m is an integer from 0 to 34, p, q, r and s are the same or different and are integers from 1 to 6, and Q is (BL)y where the bonds between L and A or B are carbon-nitrogen bonds formed by quaternization of the tertiary amine functions of A and B by the organic dihalides from which L is derived and w is 0 or 1 which are obtained by first forming a block of units by reacting a monomer of the formula II

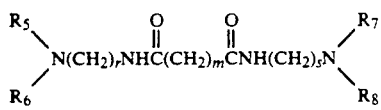

wherein each of $R_5$, $R_6$, $R_7$, and $R_8$ may be the same or different and is selected from the group consisting of $C_{1-3}$ alkyl, $C_{1-3}$ hydroxy alkyl and polyoxyalkylene, with a molar excess of a dihalide of the formula:

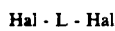

wherein Hal represent a halogen atom and L is selected from $-_2CH_2-O-_2CH_2-$, $-_2CH_2-O-_2CH_2-O-_2CH_2-$, 6.5 and more paarticularly at pH's above 7. It appears that $-(CH_2)t-$ and $-CH_2CHOHCH_2-$ where t is an integer from 2 to 6 and thereafter reacting the product so formed with a compound of the formula III

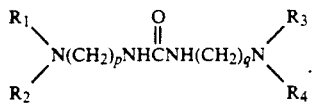

wherein $R_1$, $R_2$, $R_3$, and $R_4$, are each individually selected from the group consisting of $C_{1-3}$ hydroxyalkyl and polyoxyalkylene and p, and q are each individually integers of from 1 to 6 and, if necessary, in order to ensure a total molar ratio of compounds of Formulae II and III to those of the formula Hal - L - Hal of 1:1, reacting the product with further compound of the formula Hal - L - Hal.

11. An aqueous composition according to claim 10 wherein in said block copolymer the ratio of B to A units is in the range 0.66 to 19:1.

12. An aqueous composition according to claim 10 wherein in said block copolymer the ratio of B to A units is in the range 3 to 9:1.

13. An aqueous composition according to claim 10 wherein $R_5$, $R_6$, $R_7$ an $R_8$ are each selected from methyl and ethyl.

14. An aqueous composition according to claim 10 wherein r and s are from 2 to 4.

15. An aqueous composition according to claim 10 wherein m is from 4 to 7.

16. An aqueous composition according to claim 10 which comprises a repeating unit of the formula

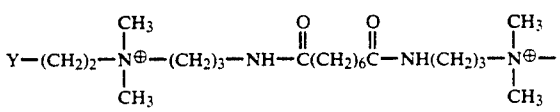

wherein Y $(CH_2)_2O$.

17. An aqueous composition according to claim 10 wherein $R_1$, $R_2$, $R_3$ and $R_4$ are each methyl or ethyl.

18. An aqueous composition according to claim 10 wherein p and q are each from 2 to 4.

19. An aqueous composition according to claim 1 wherein the smectite was sheared after admixture with the quaternary ammonium polymer.

20. An aqueous composition according to claim 1 wherein the smectite has been subjected to shear prior to admixture with the quaternary ammonium polymer.

21. An aqueous composition according to claim 1 wherein the ratio of sheared smectite to quaternary ammonium polymer is in the range of 1 to 20:1 by weight.

22. A latex paint formulation containing a thickening agent as claimed in claim 1.

* * * * *